United States Patent [19]

Chin et al.

[11] Patent Number: 5,612,046
[45] Date of Patent: Mar. 18, 1997

[54] PRODUCTION OF SHAPED BODIES WHICH HAVE FUNGICIDAL AND INSECTICIDAL PROPERTIES

[75] Inventors: Chen-Woo Chin, Wheelers Hill; Christopher N. McEvoy, Mt. Martha, both of Australia

[73] Assignee: Saneish Pty Ltd., Victoria, Australia

[21] Appl. No.: 133,098

[22] PCT Filed: Apr. 10, 1992

[86] PCT No.: PCT/AU92/00161

§ 371 Date: Mar. 28, 1994

§ 102(e) Date: Mar. 28, 1994

[87] PCT Pub. No.: WO92/18007

PCT Pub. Date: Oct. 29, 1992

[30] Foreign Application Priority Data

Apr. 12, 1991 [AU] Australia ................. PK5605

[51] Int. Cl.$^6$ ....................... A01N 25/00
[52] U.S. Cl. .................... 424/405; 424/409
[58] Field of Search ................. 424/657, 405, 424/658, 659, 660, 673

[56] References Cited

U.S. PATENT DOCUMENTS 3,247,059  4/1966  Bauer ..................... 167/38.6
4,778,833  10/1988  Van der Drift et al. ........ 523/177

*Primary Examiner*—Thurman K. Page
*Assistant Examiner*—Sharon Howard
*Attorney, Agent, or Firm*—Jensen & Puntigam, P.S.

[57] ABSTRACT

A wood preservative insert for insertion into wooden structures and a process for producing those inserts. Water is added to a dry mixture comprising at least one boron compound and at least one fluorine compound and the resulting hydration reaction binds the wood preservatives together and, once dried, results in a wood preservative insert which dissolves only on contact with moisture and has sufficient strength to be easily handled.

17 Claims, No Drawings

PRODUCTION OF SHAPED BODIES WHICH HAVE FUNGICIDAL AND INSECTICIDAL PROPERTIES

TECHNICAL FIELD

This invention relates to the production of compounds which have fungicidal and insecticidal properties and their use in wooden or timber structures to combat fungal and insect deterioration.

BACKGROUND OF THE INVENTION

The service life of wooden structures is greatly reduced by biodegradation processes caused by fungal decay such as soft rot, white and brown rot and attack by insects such as damp wood and dry wood termites. It is therefore desirable to treat wooden structures in some way to combat biodegradation to greatly increase their service life.

It has been found that the service life of wooden structures, can be considerably increased if they are inspected regularly and given remedial chemical treatment. Various methods of remedial treatment of wooden structures have been used and include the pouring of treatment liquids such creosote onto the external surface of the wooden structure or the application of bandages containing preservatives. While both of these methods are effective, they have gained only limited acceptance because they are messy and much of the chemical is lost to the environment.

The introduction of diffusible biocides into the interior of a pole should be an effective way of preventing or delaying deterioration but this method has not become a routine procedure because materials and a delivery system which is cost effective are not available.

Australian Patent No. 527,240 discloses the use of a fused monolithic body of boric oxide which dissolves over an extended period into the moisture present in the wood structure to form solution toxic to organisms responsible for decay. As the shaped monolithic bodies are formed by a melt extrusion process in excess of 1000° C., practical processing problems arise and the use of these bodies has consequently not gained wide acceptance, due to their high cost in addition they are extremely slow release and can take many years to fully dissolve even in wood with moisture content in excess of 25%.

U.S. Pat. No. 4,661,157 discloses the use of boron compounds capable of binding with water by hydration to form shaped bodies. The hydration of boron compounds by the method in the above U.S. Patent occurs quickly and results in a product relatively low in density and strength. The above patent suggests the mixing of the boron compounds with various carrier materials to increase the strength but this also has the effect of reducing the relative proportion of active ingredients in the rods and consequently the effectiveness of the shaped bodies.

SUMMARY OF THE INVENTION

The applicant has found that a stronger and denser rod can be formed by the hydration of a mixture of boron and fluorine compounds. Accordingly the invention provides a process for the production of a shaped body for use as a wood preservative insert comprising the steps of mixing together at least one hydratable boron compound and at least one fluorine compound, to form a dry mixture and adding water to said mixture to form a paste, shaping the paste and allowing the paste to set to form the shaped body.

The addition of the fluorine compound which is itself a biocide enables the hydration reaction to be more easily controlled. A slower rate of reaction and longer reaction time results in a denser and stronger shaped body. Consequently, additive materials are not required to increase the strength or density of the shaped bodies but may be added if required.

Fluoroborate complexes are also produced by the reaction of boron compounds with fluorine compounds. The complexes are also capable of hydrating and have the advantage of exhibiting lower mammalian toxicity.

After the paste is shaped it may be cooled to slow the rate of the hydration reaction to a rate which will provide a product with the desired properties. By controlling the rate of hydration the final strength and density properties of the shaped bodies can be controlled.

In accordance with another aspect of the invention, there is provided a shaped body for use as a wood preservative insert comprising at least one boron compound and at least one fluorine compound.

The boron compounds are preferably at least one of the group comprising disodium octoborate, borax (disodium tetraborate decahydrate), disodium metaborate tetrahydrate, boric acid and zinc borate.

The fluorine compound is preferably at least one of the group comprising sodium fluoride, zinc silico fluoride, potassium fluoride, ammonium hydrogen fluoride, magnesium silico fluoride, and potassium hydrogen fluoride.

PREFERRED EMBODIMENT It is preferred that the proportion of boron compound to fluorine compound is in the range of 2:1 to 3:1.

The foregoing and other features objects and advantages of the present invention will become more apparent from the following description of the preferred embodiment.

The shaped bodies in accordance with the invention are produced by first mixing a boron compound which is capable of hydrating with a fluorine compound. The boron compound preferably is at least one of the compounds in a group comprising disodium octoborate tetrahydrate, borax (disodium tetraborate decahydrate), disodium tetraborate pentahydrate, sodium metaborate tetrahydrate, boric acid and zinc borate, with disodium octoborate tetrahydrate being the most preferred.

The fluorine compound is preferably at least one of a group comprising sodium fluoride, zinc silico fluoride, potassium fluoride, ammonium hydrogen fluoride, magnesium silica fluoride and potassium hydrogen fluoride with sodium fluoride being the most preferred. Sodium fluoride has a lower water solubility and therefore will provide longer term protection to the wooden structure than a boron compound alone.

The ratio of the boron compound to the fluorine compound is in the range of 2–3:1 with a preferred ratio of 2.4:1.

To the dry mixture a structuring agent may be added such as fumed silica, clay, bentonite, colloidal or calcium carbonate in an amount from 0.05 to 0.5 wt % based on the wt of dry mixture. Preferred colloidal calcium carbonate of 0.1 wt %.

The powder phase is then mixed thoroughly for up to 5 minutes (preferably 2 minutes).

Prior to the water being added to the powder mixture, a wetting agent is added to the water to form the water phase and allowed to age for a minimum of 1 hour. The wetting agent may be a nonionic, cationic or anionic type and added in an amount of between 0.01 to 0.1 wt % based on the amount of water. The preferred wetting agent is Lutensit APS added in an amount of 0.05 wt %.

Immediately prior to adding the water phase into the premixed powder phase, its temperature should be within the range of 10°–40° C. preferably 30° C.

The water phase is then added to the powder phase in a ratio between 2:1 to 4:1 (preferably 2.8:1) and mixed for about 1–5 minutes (preferably 4 minutes). The mixing time allows sufficient time for the hydration reaction to take place and due to the exothermic nature of the reaction, an increase in mixture temperature is experienced.

The mixture in the form of a watering paste is then immediately poured into split plastic moulds.

As the temperature of the mixture and the rate of hydration within the split plastic moulds can have an effect on the final strength of the product, the filled moulds are immediately transferred to a cold room operating at a temperature in the range of about 1°–10° C. and preferably 3° C. By transferring the moulds to the cold room, the hydration reaction is slowed down and the temperature increase of the hydrating mixture is reduced.

The presence of the fluorine compound slows the rate of hydration of the boron compound to a level whereby the reaction can be adequately controlled to produce a consistent product utilising this simple process.

Solidification of the product follows after the hydration reaction is substantially complete and optimum hardness of the shaped bodies is achieved after a minimum of two hours in the cold room.

The split plastic moulds are preferably manufactured by a vacuum forming process from a PVC plastic of about 0.25–1.00 mm thick. Plastic backings are glued to the moulds to provide rigidity strength and flexibility. Locating lugs are built into each half of the mould to ensure the correct lining up of each shape. The moulds are paired then clamped together in banks of 30 to 40 sets prior to filling.

The products produced from the moulds are preferably rods of diameter ranging from 5 mm to 25 mm with length of 10 mm to 200 min.

The principle elements required for any biodegradation of wood structure are moisture (generally above about 20%) nutrients and air. Consequently wood structures are most susceptible to fungal decay and termite attack at the ground level.

To treat a wooden structure using the shaped bodies of the present invention abaxial holes are drilled in the structure starting above the groundline and extending to below the groundline.

A number of shaped bodies preferably as rods are inserted into each drilled hole and the holes are then sealed.

The moisture in the wood at ground level, slowly dissolves the chemicals in the rods and these chemicals are absorbed into the wood to prevent fungal decay and termite attack.

We claim:

1. A molded, solid wood preservative insert for insertion into a cavity of a wooden structure, comprising:

a solid insert member, consisting essentially of at least one boron compound and at least one fluorine compound, said at least one boron compound and at least one fluorine compound being bonded together by a hydration reaction such that in the presence of moisture while positioned in the wooden structure, the solid insert member will dissolve and be absorbed into the wooden structure.

2. The wood preservative insert in accordance with claim 1 wherein said at least one boron compound is selected from the group consisting of disodium octoborate, borax, disodium metaborate, disodium tetraborate, boric acid and zinc borate.

3. The wood preservative insert in accordance with claim 1 wherein the at least one fluorine compound is selected from the group consisting of sodium fluoride, zinc silico fluoride, potassium fluoride, ammonium hydrogen fluoride, magnesium silico fluoride and potassium hydrogen fluoride.

4. The wood preservative insert in accordance with claim 1 wherein the ratio of boron compound to fluorine compound is in the range of between 2:1 to 3:1.

5. The wood preservative insert in accordance with claim 1 further comprising a structuring agent.

6. A process for the production of a wood preservative insert consisting essentially of at least one boron compound and at least one fluorine compound comprising the steps of mixing together at least one boron compound and at least one fluorine compound to form a hydratable dry mixture consisting essentially of said at least one boron compound and said at least one fluorine compound, adding a water phase to said mixture to form a paste and to hydrate the dry mixture, and shaping the paste and allowing the paste to set to form said wood preservative insert.

7. The process in accordance with claim 6 wherein the strength of the wood preservative insert is controlled by allowing the paste to set in an atmosphere at a temperature between about 1° to 10° C.

8. The process in accordance with claim 6 wherein the water phase also comprises a wetting agent.

9. The process in accordance with claim 6, wherein the boron compound is selected from the group consisting of disodium octoborate, borax, disodium metaborate, disodium tetraborate, boric acid and zinc borate.

10. The process in accordance with claim 6 wherein the fluorine compound is selected from the group comprising sodium fluoride, zinc silico fluoride, potassium fluoride, ammonium hydrogen fluoride, magnesium silico fluoride and potassium hydrogen fluoride.

11. The process in accordance with claim 6 wherein the ratio of boron compound to fluorine compound is in the range of 2:1 to 3:1.

12. The wood preservatives insert in accordance with claim 2, wherein the at least one fluorine compound is selected from the group comprising sodium fluoride, zinc silico fluoride, potassium fluoride, ammonium hydrogen fluoride, magnesium silico fluoride and potassium hydrogen fluoride.

13. The process in accordance with claim 8, wherein the boron compound is selected from the group consisting of disodium octoborate, borax, disodium metaborate, disodium tetraborate, boric acid and zinc borate.

14. The process in accordance with claim 8, wherein the fluorine compound is selected from the group comprising sodium fluoride, zinc silico fluoride, potassium fluoride, ammonium hydrogen fluoride, magnesium silico fluoride and potassium hydrogen fluoride.

15. The process in accordance with claim 8, wherein the ratio of boron compound to fluorine compound is in the range of 2:1 to 3:1.

16. The wood preservative insert in accordance with claim 1, wherein the at least one boron compound is hydratable.

17. The process in accordance with claim 6, wherein the at least one boron compound is hydratable.

* * * * *